(12) United States Patent
Jaworski et al.

(10) Patent No.: US 8,957,013 B2
(45) Date of Patent: Feb. 17, 2015

(54) RECEPTORS USEFUL FOR GAS PHASE CHEMICAL SENSING

(75) Inventors: Justyn W. Jaworski, Berkeley, CA (US); Seung-Wuk Lee, Walnut Creek, CA (US); Arunava Majumdar, Orinda, CA (US); Digvijay A. Raorane, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 854 days.

(21) Appl. No.: 12/578,428

(22) Filed: Oct. 13, 2009

(65) Prior Publication Data

US 2012/0108450 A1    May 3, 2012

Related U.S. Application Data

(63) Continuation of application No. PCT/US2008/060260, filed on Apr. 14, 2008.

(60) Provisional application No. 61/032,770, filed on Feb. 29, 2008, provisional application No. 60/911,760, filed on Apr. 13, 2007.

(51) Int. Cl.
| | | |
|---|---|---|
| *G01N 25/50* | (2006.01) | |
| *G01N 33/22* | (2006.01) | |
| *C40B 40/10* | (2006.01) | |
| *C07K 7/06* | (2006.01) | |
| *C07K 7/08* | (2006.01) | |
| *C40B 30/04* | (2006.01) | |
| *C40B 60/12* | (2006.01) | |
| *G01N 33/566* | (2006.01) | |
| *A61K 38/00* | (2006.01) | |

(52) U.S. Cl.
CPC . *C40B 40/10* (2013.01); *C07K 7/06* (2013.01); *C07K 7/08* (2013.01); *C40B 30/04* (2013.01); *C40B 60/12* (2013.01); *G01N 33/566* (2013.01)
USPC ............ 514/1.1; 149/69; 149/107; 514/21.4; 514/21.5; 514/21.6; 514/21.7; 514/21.8

(58) Field of Classification Search
CPC .................................................. G01N 24/084
See application file for complete search history.

(56) References Cited

U.S. PATENT DOCUMENTS

| 6,573,107 B1 | 6/2003 | Bowen et al. | |
|---|---|---|---|
| 6,602,685 B1 | 8/2003 | Lohse | |
| 7,029,516 B2 | 4/2006 | Campbell et al. | |
| 2005/0147605 A1* | 7/2005 | Rosen | 424/143.1 |
| 2005/0255491 A1* | 11/2005 | Lee et al. | 435/6 |

FOREIGN PATENT DOCUMENTS

| WO | 98/01555 A2 | 1/1998 |
|---|---|---|
| WO | 2006/069263 A1 | 6/2006 |

OTHER PUBLICATIONS

Lim et al. (Jan. 2007) Nanomechanical Chemical Sensor Platform, Procedding of the 2nd IEEE international conference, Bangkok, Thailand, pp. 886-889.*
Larrascosa et al. (2006) Nanomechanical biosensors: a new sensing tool, Trends Anal. Chem., vol. 25, No. 3, pp. 196-206.*
Looger et al. (20030 Computational design of receptor and sensor proteins with novel functions, Nature, vol. 423, pp. 185-190.*
Cai, Q et al. (2000). "Vapor Recognition with an Integrated Array of Polymer-Coated Flexural Plate Wave Sensors,"Sensors and Actuators B 62:121-130.
Freund, M. S. et al. (Mar. 1995). "A Chemically Diverse Conducting Polymer-Based "Electronic Nose", " Proceedings of the National Academy of Sciences of the United States of America 92:2652-2656.
Goldman, E. R. et al. (2002). "Selection of Phage Displayed Peptides for the Detection of 2,4,6-Trinitrotoluene in Seawater," Analytica Chimica Acta 457:13-19.
International Search Report and Written Opinion mailed May 29, 2009, for PCT Application No. PCT/US08/60260 filed Apr. 14, 2008, 14 pages.
Kannan, B. et al. (2006). "Lithographic Techniques and Surface Chemistries for the Fabrication of PEG-Passivated Protein Microarrays," Biosensors and Bioelectronics 21:1960-1967.
Legin, A. et al. (2000). "Application of Electronic Tongue for Qualitative and Quantitative Analysis of Complex Liquid Media," Sensors and Actuators B 65:232-234.
Lim, S. et al. (2006). "Nano-Chemo-Mechanical Sensor Array Platform for High-Throughput Chemical Analysis," Sensors and Actuators B 119:466-474.
Lonergan, M. C. et al. (1996). "Array Rased Vapor Sensing Using Chemically Sensitive, Carbon Black-Polymer Resistors," Chemistry of Materials 8(9):2298-2312.
Park, J. et al. (Sep. 1, 1999). "Vapor Recognition with Small Arrays of Polymer-Coated Microsensors. A Comprehensive Analysis," Analytical Chemistry 71(17):3877-3886.
Pinnaduwagwe, L.A. et al. (Aug. 18, 2003). "Sensitive Detection of Plastic Explosives with Self-Assembled Monoloayer-Coated Microcantilevers," Applied Physics Letters 83(7):1471-1473.
Rose, A. et al. (Apr. 14, 2005). "Sensitivity Gains in Chemosensing by Lasing Action in Organic Polymers," Nature 434:876-879.
Satyanarayana, S. et al. (2006). "Parylene Micro Membrane Capacitive Sensor Array for Chemical and Biological Sensing," Sensors and Actuators B 115:494-502.

(Continued)

*Primary Examiner* — Manjunath Rao
*Assistant Examiner* — Samuel Liu
(74) *Attorney, Agent, or Firm* — Robin C. Chiang; Lawrence Berkeley National Laboratory

(57) ABSTRACT

The invention provides for a receptor, capable of binding to a target molecule, linked to a hygroscopic polymer or hydrogel; and the use of this receptor in a device for detecting the target molecule in a gaseous and/or liquid phase. The invention also provides for a method for detecting the presence of a target molecule in the gas phase using the device. In particular, the receptor can be a peptide capable of binding a 2,4,6-trinitrotoluene (TNT) or 2,4,-dinitrotoluene (DNT).

5 Claims, 6 Drawing Sheets

(56) References Cited

OTHER PUBLICATIONS

Severin, E. J. et al. (Feb. 15, 2000). "An Investigation of the Concentration Dependence and Response to Analyte Mixtures of Carbon Black/Insulating Organic Polymer Composite Vapor Detectors," Analytical Chemistry 72 (4):658-668.

Takahashi, M. et al. (2000). "Peptide Design Based on an Antibody Complementarity-Determining Region (CDR): Construction of Porphyrin-Binding Peptides and their Affinity Maturation by a Combinatorial Method," Chemistry-A European Journal 6(17):3196-3203.

UniProt. (Entered May 16, 2006). "Q1R0A5 Tfp Pilus Assembly Protein PilW-Like Protein," available at http://www.uniprot.org/uniprot/q1r0a5, 3 pages.

Vlasov, Y. G. et al. (2000). "Electronic Tongue-New Analytical Tool for Liquid Analysis on the Basis of Non-Specific Sensors and Methods of Pattern Recognition," Sensors and Actuators B 65:235-236.

\* cited by examiner

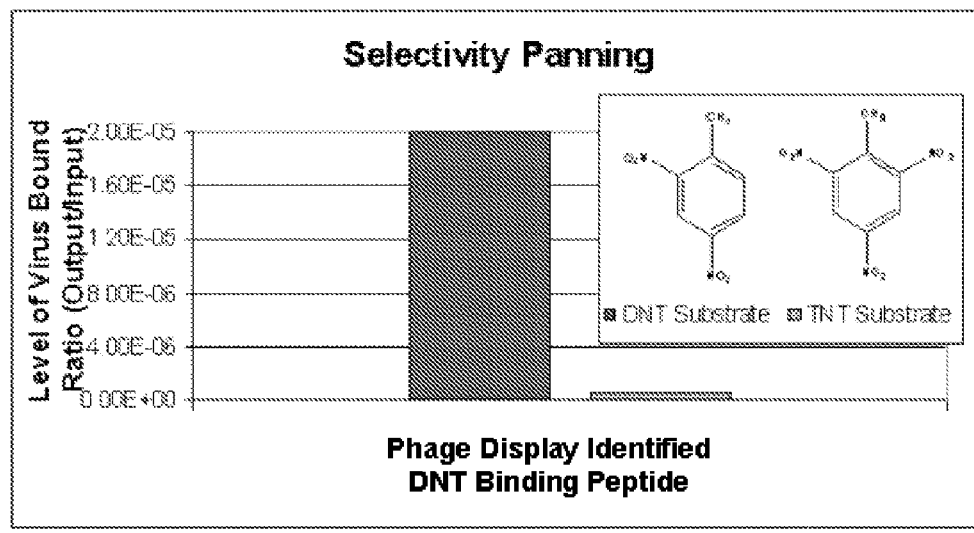
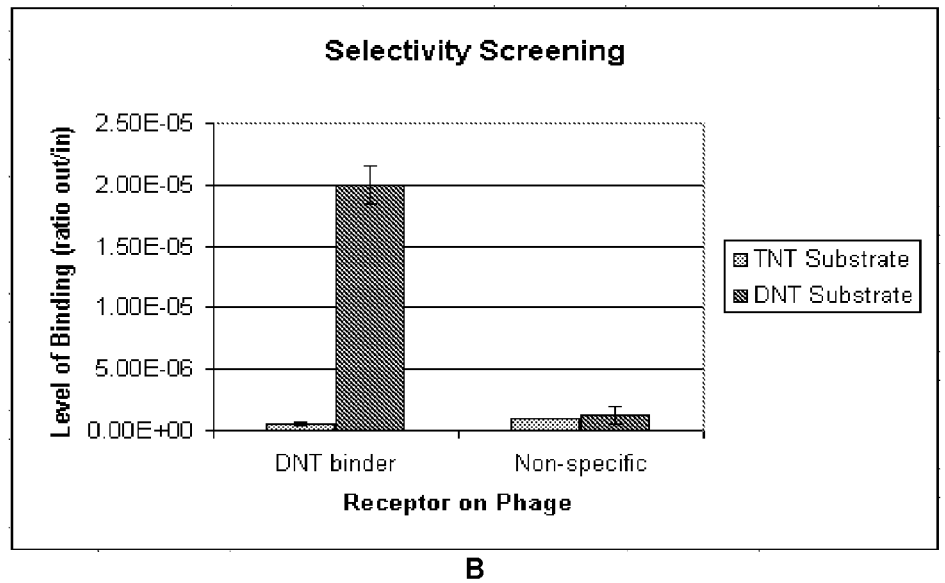
Figure 5

| Peptide Name | N term | | | | | | | Amino Acid | | | | | | | | C term |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| TNT Binder | Trp | His | Trp | Gln | Arg | Pro | Leu | Met | Pro | Val | Ser | Ile | Gly | Gly | Gly | Lys-Biotin |
| Trp(1) Knockout | Ala | His | Trp | Gln | Arg | Pro | Leu | Met | Pro | Val | Ser | Ile | Gly | Gly | Gly | Lys-Biotin |
| His Knockout | Trp | Ala | Trp | Gln | Arg | Pro | Leu | Met | Pro | Val | Ser | Ile | Gly | Gly | Gly | Lys-Biotin |
| Trp(2) Knockout | Trp | His | Ala | Gln | Arg | Pro | Leu | Met | Pro | Val | Ser | Ile | Gly | Gly | Gly | Lys-Biotin |
| Gln Knockout | Trp | His | Trp | Ala | Arg | Pro | Leu | Met | Pro | Val | Ser | Ile | Gly | Gly | Gly | Lys-Biotin |
| Arg Knockout | Trp | His | Trp | Gln | Ala | Pro | Leu | Met | Pro | Val | Ser | Ile | Gly | Gly | Gly | Lys-Biotin |
| Outer Motif Only | | | | | | | Trp | His | Trp | Gln | Arg | Pro | Gly | Gly | Gly | Lys-Biotin |
| Scrambled | Leu | Pro | Ser | Met | Arg | Val | Trp | Pro | Gln | Trp | Ile | Pro | Gly | Gly | Gly | Lys-Biotin |
| Anderson Control | Trp | His | Arg | Thr | Pro | Ser | Thr | Leu | Trp | Gly | Val | Ile | Gly | Gly | Gly | Lys-Biotin |

A

TNT Substrate Binding Assay (Normalized to BSA Signal)

B

DNT Substrate Binding Assay (Normalized to BSA Signal)

RECEPTORS USEFUL FOR GAS PHASE CHEMICAL SENSING

CROSS-REFERENCE TO RELATED APPLICATIONS

This application claims priority as a continuation application to International Patent Application No. PCT/US2008/060260, filed Apr. 14, 2008, which claims priority to U.S. Provisional Application Ser. Nos. 61/032,770, filed Feb. 29, 2008, and 60/911,760, filed Apr. 13, 2007, all of which are hereby incorporated by reference.

STATEMENT OF GOVERNMENTAL SUPPORT

The invention described and claimed herein was made in part utilizing funds supplied by the U.S. Department of Energy under Contract No. DE-AC02-05CH11231. The government has certain rights in this invention.

FIELD OF THE INVENTION

This invention relates generally to chemical sensing, and, more specifically, to gas phase sensing of trinitrotoluene (TNT) or dinitrotoluene (DNT).

BACKGROUND OF THE INVENTION

Currently, there are efforts to build "electronic tongue" sensors capable of sensing chemicals in complex liquids, and vapor sensors for sensing organic vapor using polymer-coated surface acoustic wave (SAW) sensors (Grate, Chem. Rev., vol. 1000, pp. 2627-48, 2000; Rose et al, Nature, vol. 434, pp. 876-9, 2005). However, there is no sensor available with a sufficiently high sensitivity for the detection of explosives and chemical warfare agents, as well as environmental contaminants, and in general all volatile and semi-volatile molecules. The biggest challenge is the identification of a receptor with a high binding specificity to its respective target molecule against a background of various interfering agents.

SUMMARY OF THE INVENTION

The invention provides for a composition comprising a receptor linked to a hygroscopic polymer or hydrogel wherein the receptor is capable of binding to a target molecule.

The invention also provides for a device for detecting the presence of a target molecule comprising: (a) a receptor linked to a hygroscopic polymer or hydrogel wherein the receptor is capable of binding to the target molecule, and (b) a means for sensing the binding of the target molecule and the receptor.

The invention also provides for a method for detecting the presence of a target molecule comprising: exposing a device to a sample; wherein the device comprises (1) a receptor linked to a hygroscopic polymer or hydrogel wherein the receptor is capable of binding to the target molecule, and (2) a means for sensing the binding of the target molecule and the receptor; such that any target molecule present in the sample is detected by the device.

The invention further provides for a peptide capable of binding to a 2,4,6-trinitrotoluene (TNT) or 2,4-dinitrotoluene (DNT).

The invention further provides for a composition comprising a peptide linked to a hygroscopic polymer or hydrogel wherein the peptide is capable of binding to a small organic compound.

The invention further provides for a method for identifying a peptide capable of binding a small organic compound comprising: contacting a library of peptides with the small organic compound, separating a peptide that binds to the small organic compound from peptides that do not bind to the small organic compound, amplifying the peptide that bound to the small organic compound, and identifying the peptide that bound to the small organic compound; such that the peptide capable of binding the small organic compound is identified, and with the provisio that if the small organic compound is 2,4,6-trinitrobenzene (TNB) then the library is not a combinatorial phage library.

BRIEF DESCRIPTION OF THE DRAWINGS

The foregoing aspects and others will be readily appreciated by the skilled artisan from the following description of illustrative embodiments when read in conjunction with the accompanying drawings.

FIG. 5 shows the selectivity experiments. Panel A depicts the results of a selectivity experiment of sample JHD5-11 (having amino acid sequence: HPNFSKYILHQR (SEQ ID NO:61)) panned against DNT as well as TNT targets. Panel B depicts the results of a selectivity experiment also using sample JHD5-11.

FIG. 6 shows the results of the alanine replacement experiment. Panel A depicts the amino acid residues of a TNT binding sequence and the sequences with altered residues: TNT Binder, SEQ ID NO 75; Trp(1) Knockout, SEQ ID NO:83; His Knockout, SEQ ID NO:84; Trp(2) Knockout, SEQ ID NO:85; Gln Knockout, SEQ ID NO:86; Arg Knockout, SEQ ID NO:87; Outer Motif Only, SEQ ID NO:88; Scrambled, SEQ ID NO:89; and, Anderson Control, SEQ ID NO:90. Panel B depicts the binding assay for a TNT binding peptide. Panel C depicts the binding assay for a DNT binding peptide. "RFU" refers to "relative fluorescence unit".

DETAILED DESCRIPTION

Figure 1:
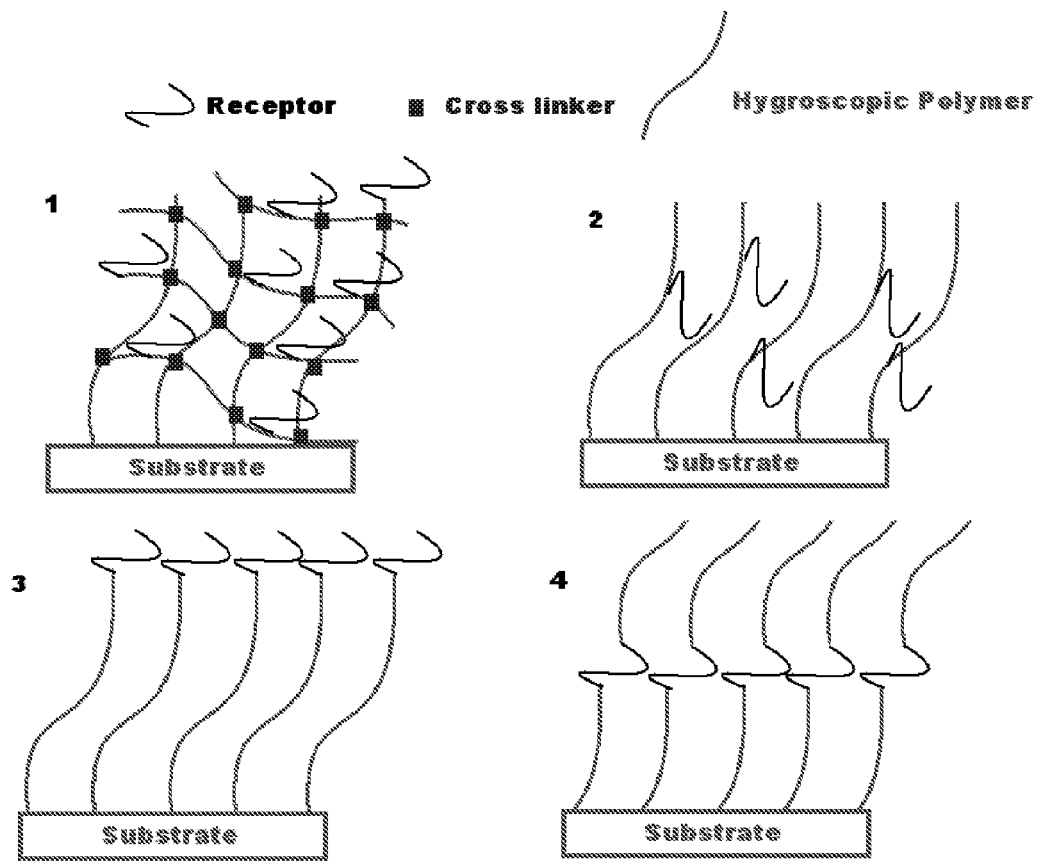
FIG. 1 shows the various possible configurations of the sensor coating layer. Panel A depicts a cross-linked mesh configuration. Panel B depicts a branched linear configuration. Panel C depicts an end-attached linear configuration. Panel D depicts an embedded linear configuration.
Figure 2:
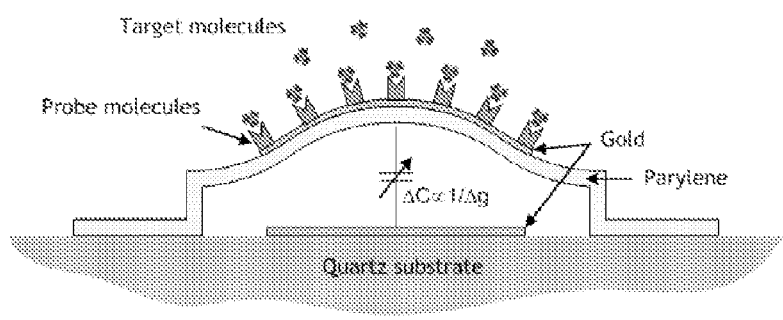
FIG. 2 shows a micromembrane surface stress sensor. "Probe molecule" refers to the receptor linked the hygroscopic polymer.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a peptide" includes a plurality of such peptides, and so forth.

These and other objects, advantages, and features of the invention will become apparent to those persons skilled in the art upon reading the details of the invention as more fully described below.

Receptors Linked to a Hygroscopic Polymer or Hydrogel

The invention provides for a composition comprising a receptor linked to a hygroscopic polymer or hydrogel wherein the receptor is capable of binding to a target molecule. The receptor linked to a hygroscopic polymer is isolated or man-made (i.e., not naturally occurring). The target molecule is any molecule or compound capable of being in a gaseous and/in liquid phase. The target molecule can be in a gaseous or liquid sample. In some embodiments, the target molecule is a gaseous phase at about 1 atmospheric pressure and at a temperature of about room temperature or 25° C. Only a minute quantity of the target molecule need be in the gaseous phase. The gaseous concentration of the target molecule is at least 1 part per trillion (ppt). In some embodiments, the gaseous concentration of the target molecule is at least 10 or 100 ppt. In certain embodiments, the gaseous concentration of the target molecule is at least 1 or 10 parts per billion (ppb).

The invention also provides for a composition comprising a receptor linked to a hygroscopic polymer or hydrogel wherein the receptor is capable of binding to a target molecule, wherein the hygroscopic polymer or hydrogel is bound by one or more water molecules. In some embodiments, the hygroscopic polymer or hydrogel is bound by the maximum number of water molecules possible for the hygroscopic polymer or hydrogel.

The receptor is any molecule capable of specifically binding to one or more target molecules. In some embodiments of the invention, the receptor is an organic compound capable of linking to the hygroscopic polymer or hydrogel. The receptor can be a protein, peptide, nucleic acid, carbohydrate, or lipid. The receptor can be obtained from nature or be synthesized. The use of the terms "binding" or "bind" to describe the interaction between the receptor and target molecule means the association of the receptor and target molecule through such interactions as hydrogen bonding, var der Waal interaction, hydrophobic interaction, pi-pi interaction, and the like.

The intended target molecules of a receptor may be a combination of different but related molecules, such as analogs. In some embodiments of the invention, the target molecule is a small organic compound. Typically the small organic compound has a molecular weight of no more than 1,000 daltons. In some embodiments, the small compound has a molecular weight of no more than 500 daltons. In certain embodiments, the small compound has a molecular weight of no more than 250 daltons. In some embodiments, the small compound has a molecular weight of at least 50, 100, 150, or 200 daltons.

The hygroscopic polymer or hydrogel is any structure that: does not substantially interfere with the binding of the receptor with the target molecule, and is capable of absorbing water molecules from the atmosphere and/or retaining water molecules in its proximity. The hygroscopic polymer or hydrogel prevents the fouling of the environment of the receptor with molecules other than the target molecule that would interfere with the binding of the binding and the target molecule. The hygroscopic polymer is defined to also include monomers. Hygroscopic polymers or hydrogels may comprise structures capable of hydrogen bonding with one or more water molecules. Water molecules preferentially bond with the hydroscopic polymer or hydrogel than to go into the gaseous phase. Structures capable of hydrogen bonding include ethers.

The hygroscopic polymer or hydrogel can absorb water vapor present in air known as deliquescence. The hygroscopic polymer can be a polymer comprising from 1 to 40 mers. In some embodiments, the polymer can comprise from 2 to 30 mers. In certain embodiments, the polymer can comprise 2 to 10 mers. The hygroscopic polymer can comprise one or more hydrophilic structures or groups (such as, hydroxyl groups, amines, carboxyl groups, ether bonds, ester bonds, and the like), or combination thereof. The hygroscopic polymer has an affinity to form hydrogen bonds with water molecules. Exemplary hygroscopic polymers include polyethylene glycols (PEG), agarose, poly(2-acrylamido-2-methyl-1-propanesulfonic acid, poly(2-hydroxyethyl methacrylate), polypentaerythritol ethoxylate, poly(N,N-dimethyl-3,5, dimethylene) piperidium chloride, quaternized polyimidazoline, polyacrylamide, and combinations thereof. Other hygroscopic polymers are described in U.S. Pat. No. 7,029,516, which is hereby incorporated by reference in its entirety.

When the hygroscopic polymer is PEG, the molecular weight of PEG can be determined from the equation 44*n+18 (g/mol), wherein "n" is the number of monomers. With this equation the molecular weight of the monolayer hygroscopic regions may range from 62 g/mol for a monomer to approx 1800 g/mol for a 40 mer.

The hygroscopic polymer can be a linear or branched chain of monomers. The receptor may be linked at any end or ends, or within the ends, of a linear or branched chain. The receptor may be linked to the hygroscopic polymer in any suitable manner that does not substantially interfere with the binding of the receptor with the target molecule, and vice versa. The receptor may be linked to the hygroscopic polymer with one or more covalent bonds.

Suitable hydrogels can comprise a network of water-insoluble polymer chains that are capable of absorbing of water. The polymers of the polymer chains can be natural or synthetic polymers. Suitable hydrogels can comprise one or more of the following: starch, dextrans, chitin, cellulose derivatives, agarose, modified agaroses, other polysaccharides, polyvinylpyrrolidone, polyvinyl alcohol, sodium polyacrylate, acrylate polymers, any copolymer with an abundance of hydrophilic groups, and the like.

Device for Detecting the Presence of a Target Molecule in the Gas Phase

The invention also provides for a device for detecting the presence of a target molecule comprising: (a) a receptor linked to a hygroscopic polymer or hydrogel wherein the receptor is capable of binding to the target molecule, and (b) a means for sensing the binding of the target molecule and the receptor.

The device of the present invention provides the receptor in an environment that comprises sufficient water molecules such that the target molecule can enter into the environment, e.g., such that the target molecule is changing from a gaseous phase into an aqueous phase. There are sufficient water molecules in the environment due to the water absorbing and/or retaining properties of hygroscopic polymer. The device can be used for detecting the target molecule in a gaseous and/or liquid phase, The device may comprise a plurality of the receptors which are configured in one or more layers. The plurality of the receptors may form a sensor coating layer. In some embodiments, the receptor-hygroscopic polymers are ordered in the same orientation. In certain embodiments, the sensor coating layer comprises a single layer (i.e., a monolayer) of receptors, wherein each receptor is linked to a hygroscopic polymer and all of the receptor-hygroscopic polymer molecules are ordered in the same orientation.

The sensor coating layer comprises the composition comprising a receptor linked to a hygroscopic polymer. The sensor coating layer can be of various configurations. Such suitable configurations include a cross-linked mesh configuration, a branched linear configuration, an end-attached linear configuration, and an embedded linear configuration.

In the cross-linked mesh configuration, the receptors are branched off from the hygroscopic polymer. The hygroscopic polymer is cross-linked to each other in order to provide a higher density of polymer as well as available receptors on the substrate. The network also maintains the receptor within where it may encounter more interactions with surrounding associated water molecules. See FIG. 1, Panel A.

In the branched linear configuration, the hygroscopic polymer is formed in a monolayer formation with individual receptors placed at points along the hygroscopic polymer backbone. The branched nature allows receptor conformational freedom while enhancing exposure to associated water molecules of the surrounding hygroscopic polymer. See FIG. 1, Panel B.

In the end-attached linear configuration, the hygroscopic polymer is formed in a monolayer formation in which the receptor is fully exposed and is not restricted in its conformation. The associated water molecules with the underlying hygroscopic polymer may interact with the top-lying receptor region to enhance gas phase binding in different humidity environments. See FIG. 1, Panel C.

In the embedded linear configuration, the hygroscopic polymer layer is formed in which a monolayer is created with an embedded receptor. This orientation may restrict the conformation availability of the receptor, though it will ensure surrounding water molecules are associated with the receptor region. See FIG. 1, Panel D.

The cross-linkage may be a direct result of the chemical structure of the hygroscopic polymer or induced by a variety of cross-linking compounds, though it may be suitable to use water soluble cross-linking compounds such as the glycidyl ether compounds or gluteraldehyde. Glycidyl ether compounds include poly propylene glycol diglycidyl ether, poly clycerin diglycidyl ether, or poly ethylene glycol diglycidyl ether. Cross-linking may be induced by moisture, UV radiation, or heat treatment. Such cross-linking procedures are well known to one of ordinary skill in the art.

There are various means for sensing the binding of the target molecule and the receptor. One means for sensing the binding of the target molecule and the receptor is micromembrane surface stress sensor. Lim et al. ("Nanomechanical Chemical Sensor Platform", IEEE-NEMS 2007 (No. 262), which is hereby incorporated by reference in its entirety) describe the making and use of a micromembrane surface stress sensor. In some embodiments, the device comprises a micromembrane surface stress sensor comprising two electrodes separated by a space wherein one of the two electrodes comprises a sensor coating layer such that the one or more receptors of the sensor coating layer binding the target molecule create steric and electrostatic repulsion which generate a surface stress on the electrode which in turn deflects the electrode thereby generating a capacitance change in the electrical sensing between the two electrodes. The membrane deflection increases the surface stress generated and also increases the separation of the two electrodes. The capacitance change can be measured with instruments well known to those of ordinary skill in the art.

In some embodiments of the device, the device further comprises a first electrode and a second electrode, wherein the receptor linked to the hydroscopic polymer or hydrogel is attached a second electrode, wherein the binding of the receptor with the target molecule causes a change in capacitance between the first and second electrodes, and the means of sensing the binding of the target molecule and the receptor is a means to measure the change in capacitance between the first and second electrodes. In certain embodiments, the binding of the receptor with the target molecule causes an increase in the distance of the first and second electrodes capacitance which in turn causes a decrease in the capacitance. In certain embodiments, the second electrode is located on a parylene membrane and the receptor linked to the hydroscopic polymer or hydrogel is attached to the second electrode on a surface of the second electrode that does not directly face the first electrode.

In some embodiments of the device, the electrode comprising the sensor coating layer is a parylene membrane and the sensor coating layer is located on the plane of the membrane facing away from the other electrode. In certain embodiments, the electrode comprising the sensor coating layer has a convex shape facing away from the other electrode. The change in capacitance can be measured using a multiplexer, function generator and lock-in amplifier.

In certain embodiments, the device comprises a fully integrated chemical sensing platform incorporating a sensing chip and all measurement circuits in a single board. The board includes a fabricated membrane sensor chip, capacitance to digital converter (CDC) chips, microprocessor, USB interface, temperature control, etc. Using the board, data acquisition speed (for each channel) of 9 samples/sec and power consumption (for data acquisition) of 17.7 mA @ 5 V can be achieved. (See Lim et al., 2007.)

The entire device can be manufactured with handheld, portable or field-deployable dimensions.

Other means for sensing the binding of the target molecule and the receptor include the use of chemo-mechanical transducers (Pinnaduwage et al., Applied Physics Lett. Vol. 83, pp. 1471-3, 2003; Thundat et al., Sensors and Sensing in Biology and Enginering. Springer-Verlag, 2003), 2-D microplexed cantilever array platforms (Lim et al., Sensors and Actuators B: Chemical, 2006), and parylene micromembrane surface stress sensors (Satyanarayana et al., Sensors and Actuators B: Chemical, vol. 115, pp. 494-502, 2005). These references are hereby all incorporated by reference in their entireties.

The device and compositions of the present invention may also be incorporated into the following sensor systems: "electronic tongue" sensors (Legin et al., Sensors and Actuators B, vol. 65, pp. 232-4, 2000; Vlasov et al., Sensors and Actuators B, vol. 65, pp. 235-6, 2000) and vapor sensors (Freund et al., Proc. Natl. Acad. Sci. USA, vol. 92, pp. 2652-6, 1995; Lonergan et al., Chem. Mater., vol. 8, pp. 2298-312, 1996; Park et al., Anal. Chem., vol. 71, pp. 3877-86, 1999; Severin et al., Anal. Chem., vol. 72, pp. 658-68, 2000; Cai et al., Sensors and Actuators B, vol. 62, pp. 121-30, 2000; Grate, Chem. Rev., vol. 1000, pp. 2627-48, 2000). These references are hereby all incorporated by reference in their entireties.

The invention also provides for a method for detecting the presence of a target molecule comprising: exposing a device to a sample; wherein the device comprises (1) a receptor linked to a hygroscopic polymer or hydrogel wherein the receptor is capable of binding to the target molecule, and (2) a means for sensing the binding of the target molecule and the receptor; such that any target molecule present in the sample is detected by the device. The sample can be a gaseous or liquid sample. In some embodiments, the sample prior to being subjected to the method is suspected of containing the target molecule.

The invention also provides for a method for detecting the presence of a target molecule using any of the devices described above.

Small Organic Compound Target Molecules

In certain embodiments the small organic compound is a substituted benzene derivative. Substituted benzene derivatives comprise at least one alkyl or one nitro functional groups. The alkyl functional group can be a methyl. In some embodiments, the substituted benzene derivatives is a nitroaromatic compound comprising at least one nitro functional group. Nitroaromatic compounds include, without limitation, 2,4,6-trinitrotoluene (TNT), 2,4-dinitrotoluene (DNT), 2,4,6-trinitrobenzene (TNB), nitrobenzene, methylnitrobenzenes, methyldinitrobenzenes, methyltrinitrobenzene, ethylnitrobenzenes, ethyldinitrobenzenes, ethyltrinitrobenzene, dinitrobenzenes, trinitrobenzenes, nitrotoluenes, dinitrotoluenes, nitroxylene, dinitroxylene, trinitroxylene, and nitrostyrene. In some embodiments, the small organic compound has a vapor pressure ranging from about $1 \times 10^{-9}$ to about $1 \times 10^{-6}$. In certain embodiments, the small organic compound has a vapor pressure ranging from about $4 \times 10^{-9}$ to about $4 \times 10^{-7}$. TNT has a vapor pressure of about $8 \times 10^{-9}$. DNT has a vapor pressure of about $2 \times 10^{-7}$. TNT has a molecular weight of about 227 daltons. DNT has a molecular weight of about 182 daltons.

Peptide Receptors

The receptor can comprise a peptide. Such a peptide comprises a sequence of amino acids, wherein the amino acids can be naturally occurring or synthetic, or modified, or a combination of thereof. The portion of the peptide that binds to the target molecule (thereafter "the binding sequence") comprises three to twenty amino acid residues. The amino acids of a binding sequence can be naturally occurring or synthetic, or modified, or a combination of thereof. In some embodiments, the binding sequence comprises three to fifteen amino acid residues. In certain embodiments the binding sequence comprises seven to twelve amino acid residues. The binding sequence can be a linear amino acid sequence or an amino acid sequence in a constrained loop. The amino acid sequence in a constrained loop when the binding sequence is flanked at each end with an amino acid with a side group comprising a thiol, and the two thiols form a disulfide bond. The amino acid with a side group comprising a thiol can be a cysteine.

The invention provides for a peptide comprising a binding sequence capable of binding a TNT molecule having an amino acid sequence comprising the following structure:

B1-B2-B3-B4-B5-B6, or any combination of one or more of B1, B2, B3, B4, B5, and B6;

wherein:

B1 comprises a proline adjacent to a methionine, leucine, alanine or an amino acid with a positively charged side group;

B2 comprises an amino acid with an aromatic side group adjacent to an amino acid with a positively charged side group;

B3 comprises any combination of two amino acids, wherein independently each amino acid is with a carboxamide side group or a positively charged side group;

B4 comprises an amino acid with an aromatic side group;

B5 comprises any combination of two amino acids with a side group capable of hydrogen bonding; and B6 comprises any combination of two amino acids with a positively charged side group.

Exemplary B1 include Pro-Leu, Leu-Pro, Met-Pro, and Pro-His. Exemplary B2 include Tip-His and Lys-Phe. Exemplary B3 include His-His, Asn-Asn, Lys-Asn, and Gln-His. Exemplary B5 include Tyr-Tyr, Ser-Thr, Thr-Thr, and Asn-Tyr. Exemplary B6 include His-His and Arg-His.

Consensus sequences found in some binding sequences of binding TNT are WHW, WHWS (SEQ ID NO:76) and WHWSXRTALYTT (wherein "X" is any amino acid) (SEQ ID NO: 77). Binding sequences capable of binding TNT are listed in Table 1.

TABLE 1

| Binding Sequences Capable of Binding TNT Amino Acid Sequence (no. of times sequence identified by phage display) | |
|---|---|
| QHQYRMG | (SEQ ID NO: 1) |
| LPMTLHR | (SEQ ID NO: 2) |
| LTLSAQG | (SEQ ID NO: 3) |
| SGAATRL | (SEQ ID NO: 4) |

TABLE 1-continued

Binding Sequences Capable of Binding TNT
Amino Acid Sequence (no. of times sequence identified by phage display)

| Sequence | SEQ ID NO | Count |
|---|---|---|
| YPNHPHR | (SEQ ID NO: 5) | |
| STSTLQK | (SEQ ID NO: 6) | |
| YPNHPHH | (SEQ ID NO: 7) | |
| STSTLQK | (SEQ ID NO: 8) | |
| GEFNNLR | (SEQ ID NO: 9) | |
| RLTDPMH | (SEQ ID NO: 10) | |
| TAPYYRN | (SEQ ID NO: 11) | (X2) |
| HNRTTLL | (SEQ ID NO: 12) | (X2) |
| NAPRTPA | (SEQ ID NO: 13) | |
| TKAHPYH | (SEQ ID NO: 14) | |
| FHYNNMH | (SEQ ID NO: 15) | (X2) |
| YPHLHSN | (SEQ ID NO: 16) | |
| LNMNHHS | (SEQ ID NO: 17) | (X3) |
| QHNYWGT | (SEQ ID NO: 18) | (X6) |
| GHTFLDT | (SEQ ID NO: 19) | |
| SVFMNTP | (SEQ ID NO: 20) | |
| TPNVVVP | (SEQ ID NO: 21) | |
| EQNHAYF | (SEQ ID NO: 22) | |
| IAQNRWI | (SEQ ID NO: 23) | |
| HQFADIY | (SEQ ID NO: 24) | |
| RTRHRQRTHSRQ | (SEQ ID NO: 25) | |
| TNNFTMTSLAPF | (SEQ ID NO: 26) | |
| TSQFTFNPPLLI | (SEQ ID NO: 27) | |
| NPPPQTEASNSF | (SEQ ID NO: 28) | |
| YRDSSKPYLHYP | (SEQ ID NO: 29) | |
| DWTLPSWYGLPR | (SEQ ID NO: 30) | |
| DSMYKQLISAPK | (SEQ ID NO: 31) | |
| ALQMKGSASALA | (SEQ ID NO: 32) | |
| YPSPMTWLATPF | (SEQ ID NO: 33) | |
| WHWQRPLMPVSI | (SEQ ID NO: 34) | |
| WHWNFKPPHDLL | (SEQ ID NO: 35) | |
| WHWSHRTALYTT | (SEQ ID NO: 36) | |
| WHWSPRTALYTT | (SEQ ID NO: 37) | |
| WHWKPPAPYVWW | (SEQ ID NO: 38) | |

The invention provides for a peptide comprising a binding sequence capable of binding a TNT molecule but not a DNT molecule.

The invention provides for a peptide comprising a binding sequence capable of binding a DNT molecule having an amino acid sequence comprising the following structure: C1-C2-C3-C4, or any combination of one or more of C1, C2, C3, and C4;

wherein:

C1 comprises any combination of two amino acids, wherein independently each amino acid is proline, alanine, or an amino acid with a side group capable of hydrogen bonding;

C2 comprises an amino acid with an aromatic side group adjacent to an amino acid with a positively charged side group;

C3 comprises two amino acids with positively charged side groups; and

C4 comprises two amino acids with side groups capable of hydrogen bonding.

Exemplary C1 include Pro-Ala, Ser-Pro, and Gln-Tyr. Exemplary C2 include Trp-His and Lys-Phe. Exemplary C3 include His-His and Arg-His. Exemplary C4 include Tyr-Tyr, Ser-Thr, Thr-Thr, and Asn-Tyr.

Consensus sequences found in some binding sequences of binding DNT are LHK, KHL, QRPTT (SEQ ID NO: 78), QRPTTQ (SEQ ID NO: 79), QRPTTXG (wherein "X" is any amino acid) (SEQ ID NO: 80), QRPTTQQG (SEQ ID NO:81) QRPTTQLG (SEQ ID NO: 82). Binding sequences capable of binding DNT are listed in Table 2.

TABLE 2

Binding Sequences Capable of Binding DNT
Amino Acid Sequence (no. of times sequence identified by phage display)

| Sequence | SEQ ID NO | Count |
|---|---|---|
| PANPSRF | (SEQ ID NO: 39) | |
| TQTVTSF | (SEQ ID NO: 40) | |
| WKEEHPG | (SEQ ID NO: 41) | |
| PMAPLWH | (SEQ ID NO: 42) | |
| TKLTPAT | (SEQ ID NO: 43) | (X2) |
| SPLSHPL | (SEQ ID NO: 44) | (X2) |
| MPTLFNK | (SEQ ID NO: 45) | |
| PTDPQKN | (SEQ ID NO: 46) | |
| SIQNTFL | (SEQ ID NO: 47) | |
| NRPWLST | (SEQ ID NO: 48) | |
| LHKGPWYTPYPL | (SEQ ID NO: 49) | (X2) |
| LHKPSPRWLPVP | (SEQ ID NO: 50) | (X2) |
| LHKTPGSYSRWS | (SEQ ID NO: 51) | |
| YHRTYTPSYDSP | (SEQ ID NO: 52) | (X3) |
| RTSSGNKTTFMS | (SEQ ID NO: 53) | |
| KIMHGHRHPLLH | (SEQ ID NO: 54) | |
| QPATISGRVRVC | (SEQ ID NO: 55) | |
| QRPTTQLGSEYA | (SEQ ID NO: 56) | |
| QRPTTQQGPSML | (SEQ ID NO: 57) | (X5) |
| TTNSDKTQGSVR | (SEQ ID NO: 58) | |
| HLNWAISLYSSP | (SEQ ID NO: 59) | |
| HLLYSAGSAVML | (SEQ ID NO: 60) | |
| HPNFSKYILHQR | (SEQ ID NO: 61) | (X4) (binding sequence also known as JHD5-11) |

TABLE 2-continued

Binding Sequences Capable of Binding DNT
Amino Acid Sequence (no. of times sequence
identified by phage display)

| | | |
|---|---|---|
| WHNSLWTTPTTT | (SEQ ID NO: 62) | |
| WPHSHLYIRTNS | (SEQ ID NO: 63) | |
| IHKHRVSAPSIT | (SEQ ID NO: 64) | |
| LHKTPGSYSRWS | (SEQ ID NO: 65) | |
| VHSHYTKHAPFR | (SEQ ID NO: 66) | |
| WHRTPSTLWGVI | (SEQ ID NO: 67) | |
| KHLDTASSRHWD | (SEQ ID NO: 68) | (X3) |
| AWVPTNTMTTLR | (SEQ ID NO: 69) | |
| QPSELPSILRPL | (SEQ ID NO: 70) | (X2) |
| ATTTLPPAPFAG | (SEQ ID NO: 71) | |
| HASVPRYPHYSM | (SEQ ID NO: 72) | |
| ASWHSHTRLNMH | (SEQ ID NO: 73) | (X13) |
| DEGHGHWYYDQR | (SEQ ID NO: 74) | (X3) |

The invention provides for a peptide comprising a binding sequence capable of binding a DNT molecule but not a TNT molecule.

Exemplary amino acids with a positively charged side group include arginine, histidine, and lysine. Exemplary amino acids with an aromatic side group include tryptophan, phenylalanine, and tyrosine. Exemplary amino acids with a carboxamide side group include glutamine and asparagines. Exemplary amino acids with a side group capable of hydrogen bonding include tyrosine, serine, threonine, glutamine, and asparagines.

The peptides that bind TNT or DNT are useful for incorporating in any device for detecting TNT or DNT. Such devices may comprise any suitable chemical sensing or molecular recognition platform, such as cantilever, surface plasmon resonance, or the like, where the peptide may operate as a recognition site for TNT or DNT. Such devices by virtue of the use of the peptides have a high selectivity for the target substrate, such as TNT or DNT, and do not bind molecules that are not the target substrate. Such devices can be used to facilitate explosive detection by detecting a small organic molecules which is an explosive, and/or compounds which result from the decomposition of an explosive, such as TNT or DNT.

The peptides may be fewer than about 50 amino acids, fewer than about 30 amino acids, or fewer than about 20 or 15. The peptides may be synthesized by the well-known Merrifield solid-phase chemical synthesis and modifications thereof method wherein amino acids are sequentially added to a growing chain, see Merrifield, J. Am. Chem. Soc., 85:2149 56 (1963). Linear peptides may be chemically synthesized by manual means or by automation in commercially available synthesis equipment. Systems for manually synthesizing peptides on polyethylene glycols are available from Cambridge Research Biochemicals, Cambridge, Mass. Automatic peptide synthesis equipment is available from suppliers, including Applied Biosystems, Inc., Foster City, Calif.; Beckman Instruments, Inc., Waldwick, N.J.; and Biosearch, Inc., San Rafael, Calif. Using such automatic synthesizers according to manufacturer's instructions, peptides may be produced in gram quantities for use in the present invention. Peptides synthesized can be isolated or purified using methods well known to those of ordinary skill in the art, such as the reverse phase HPLC method.

Analysis of Receptor Binding Constants

The binding constant of a receptor to a target molecule can be determined using isothermal titration calorimetry (ITC). ITC quantitatively measures a receptor's binding constant by titration of known amounts of the target molecule with known amounts of the receptor. ITC can be used to measure the binding constant of the TNT- or DNT-binding peptides against TNT or DNT, respectively. Suitable experimental conditions can be aqueous solutions containing 50% acetonitrile, with 2.5 mL of 10 μM of the receptor in the reservoir and the use of 100 μM target molecule solution, at 10 μL volumes, to titrate the receptor. Between each volume added, there is a 30 minute interval.

The binding constant of a receptor to a target molecule can also be determined using a thermal desorber/gas chromatography/mass spectrometer (TD/GC/MS). The peptide is immobilized onto gold coated polystyrene of silica beads. The silica are then placed in a desorption tube and the target molecule is introduced to the receptor coated beads. The chamber is purged with nitrogen gas and rapidly heated to various temperatures, and the release of the target molecules at the different temperatures is measured using the GC/MS.

Figure 3:
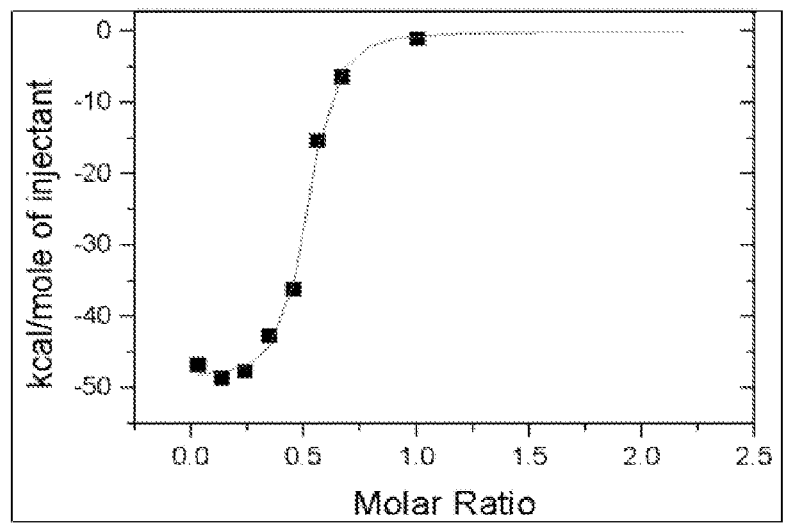
FIG. 3 shows the measurement for the Kd of peptide WHWQRPLMPVSIGGGK (SEQ ID NO:75) (biotin) and TNT.

The dissociation constant (Kd) of WHWQR-PLMPVSIGGGK (SEQ ID NO: 75) (biotin) is 71 nM as measured by from software by concentration of TNT tittered at inflection point (see FIG. 3).

The binding sequences can be further analyzed for consensus sequences and residues by synthesizing peptides identical to a known binding sequence except for the replacement or one or more residue with an amino acid with a different side group. For example, a tryptophan, histidine, glutamine, arginine, or proline can be replaced with an amino acid with an alkyl side group. Alanine is an example of such an amino acid as it has a methyl side group. These synthesized peptides can undergo affinity assays to determine their dissociation constants for comparison with the dissociation constant of the original unaltered binding sequence.

Methods of Identifying Peptides Capable of Binding a Small Organic Compound

The invention further provides for a method for identifying a peptide capable of binding a small organic compound comprising: contacting a library of peptides with the small organic compound, separating a peptide that binds to the small organic compound from peptides that do not bind to the small organic compound, amplifying the peptide that bound to the small organic compound, and identifying the peptide that bound to the small organic compound; such that the peptide capable of binding the small organic compound is identified, and the provisio that if the small organic compound is 2,4,6-trinitrobenzene (TNB) then the library is not a combinatorial phage library.

In some embodiments, the method comprises: contacting a library of combinatorial phage library comprising a library of peptides with the small organic compound, separating a phage that bound to the small organic compound from phages that do not bind to the small organic compound, amplifying the phage that bound to the small organic compound, and identifying the peptide of the phage that bound to the small organic compound; such that the peptide capable of binding the small organic compound is identified and the small organic compound is not 2,4,6-trinitrobenzene (TNB).

Figure 4:
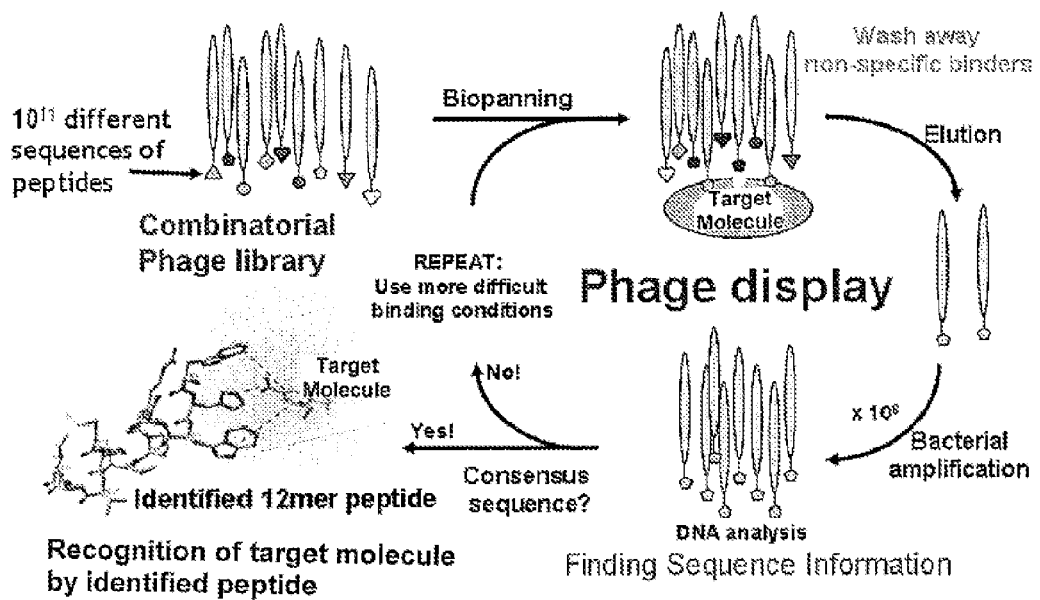
FIG. 4 shows an overview of phage display procedure.

The library of peptides can comprise or be generated from a combinatorial phage library, bacterial cell surface display library, yeast surface display library, mRNA display, or any peptide or protein based display technique. The combinatorial phage library can be a M13 bacteriophage library. The M13 bacteriophage is about 880 nm long and about 7 nm wide. Each M13 bacteriophage displays a peptide on the phage's "tail" region. In the library, each phage displays a plurality of peptides. Typically each phage displays five peptides. The peptides attached to each phage has the same amino acid sequence. Between different phages, the peptides attached to each phage is of a different amino acid sequence than the peptides attached to another phage. Each peptide can be from 3 to 20 amino acids in length, or from 7 to 12 amino acids in length. Each peptide can be in a linear structure or a constrained structure. In the constrained structure, the peptide is in a loop structure. The loop structure can be held together by a disulfide bond formed between two cysteine residues. The peptide of interest is located between these two cysteines. The library can contain about $4 \times 10^{11}$ peptides of different amino acid sequences. FIG. 4 provides an example of the use of such a method. The target molecule can be any small organic compound, such as TNT or DNT. Suitable phage libraries are commercially available from New England Biolabs Inc. (Ipswich, Mass.). In addition, the library can be constructed to insert randomized DNA sequences into the genome of a phage, such as M13 bacteriophage, using recombinant DNA techniques. Phages can be amplified by infecting a suitable bacterial host and allowing replication of the phage with the host. A suitable bacterial host for M13 bacteriophage is *E. coli*. A phage that bound to the small organic compound can be separated from phages that do not bind to the small organic compound by having the small organic compound attached to a support that is not is not removed by a wash. The support can be a solid support such as a base or beads. The wash can be any suitable buffered solution that does not alter the phage or peptides.

After the peptide or peptides of the phage that bound to the small organic compound are identified, the method can further comprise contacting the phage that bound to the small organic compound with the small organic compound, separating a phage that bound to the small organic compound from phages that do not bind to the small organic compound, amplifying the phage that bound to the small organic compound, and identifying the peptide of the phage that bound to the small organic compound. These steps can be further repeated. At each separating step, the non-specific binders are washed away with a buffer. An exemplary buffer contains 0.1% Tween, a detergent. Specifically bound phage are then eluted and captured from the target molecule using a low pH buffer. The screening is repeated several times with increasingly stringent binding conditions of increased buffer concentration, such as increased Tween concentration. Peptides identified during later rounds of identification on average have a higher binding affinity than those peptides during earlier rounds of identification.

The invention having been described, the following examples are offered to illustrate the subject invention by way of illustration, not by way of limitation.

EXAMPLE 1

Identification of Peptide Capable of Binding TNT or DNT

Target specific receptor screening for dinitrotoluene (DNT), which is the decomposition product of trinitrotoluene (TNT), is carried out using the phage display process. This screening method, depicted in FIG. 4, is utilized for the identification of DNT binding peptide receptors. The process utilizes a large combinatorial library of M13 bacteriophage expressing candidate receptors on the pIII region of their protein coat. This receptor library is comprised of variable regions 7 or 12 amino acid in length. The library of potential receptor-bearing phage is then allowed to incubate with the target molecule, such as DNT, at room temperature for 30 minutes. The non-specific binders are washed away with a buffer containing 0.1% Tween, a detergent. Specifically bound phage are eluted and captured from the target using a low pH buffer. The screening is repeated several times with increasingly stringent binding conditions of increased Tween concentration until a homologous binding motif emerges. The resulting amino acid sequence constitutes the receptor which is then created using solid-phase peptide synthesis. Using standard Fmoc chemistry, a C terminal cysteine is linked with a 6-mer of poly (ethylene glycol) followed by the identified DNT receptor motif. The C terminal cysteine provides the thiolated end-group for attachment to the gold coated membrane while the poly (ethylene glycol) is incorporated to reduce the response of the system to humidity changes. This DNT binding peptide/PEG fused polymer is utilized as the receptive layer for the present micromembrane system.

Specific recognition motif among billions of peptide candidates are identified by comparing the resulting identified peptide receptors. This identification is performed by measuring the number of phage remaining bound to the target after rigorous washing given a known initial amount of phage. The resultant best binding receptor for DNT is compared against a similar substrate of TNT which differs in the addition of only one nitro group.

Selectivity screening is performed by first binding phage (incubated with the target molecule, such as TNT, to allow binding to occur) for 30 minutes. The unbound, non-specific, and low affinity binding phage is washed away. The target molecule, such as TNT, is removed via the wash steps containing surfactant (Tween-20 in Tris-Buffered Saline). The specifically bound phage is eluted under low pH buffer where the specific binding phage is captured and their concentration (number of output phage) is determined by plating the phage with *E. coli* in a pfu counting assay.

FIG. 5, Panels A and B shows a typical panning experiment result, which reveals the selectivity of the peptide sequence for DNT over that of the TNT target. Comparative binding assay data suggests levels of binding to TNT for the DNT designed peptide (HPNFSKYILHQR; SEQ ID NO: 61) are on the order of non-specific interaction confirming that the designed peptide is indeed selective for the DNT target.

EXAMPLE 2

Alanine Scanning

Amino acid residues of a TNT binding sequence are designed to be replaced with an alanine (see FIG. 6, Panel A). The resulting amino acid sequences are synthesized using solid phase peptide synthesis. These synthesized peptides are then scanned for changes in binding ability. The results indicate that the first tryptophan residue and histidine residue of the binding sequence are critical for binding of the peptide to TNT (see FIG. 6, Panel B). Similar results for a DNT binding sequence (HPNFSKYILHQR; SEQ ID NO: 61) indicate that the first histidine residue is critical for binding of the peptide to DNT (see FIG. 6, Panel C).

EXAMPLE 3

Gas Phase Binding

Gold Chip Preparation. A (100) silicon wafer is cleaned with heated Piranha solution. A 5 nm chrome layer is thermally evaporated onto the wafer as an adhesion layer between the gold and silicon. A 25 nm thick layer of gold is then thermally evaporated onto the wafer. The wafer is then protected using 2 μm of G-line photoresist prior to dicing into 3 mm by 3 mm chips. The photoresist is then stripped using heated PRS-3000 solution, and chips are cleaned and dried.

Gas Phase Binding Assays. DNT receptors are embedded in a hygroscopic oligo (ethylene glycol) (OEG) coating to test gas phase binding. Given DNT's higher vapor pressure compared to TNT, it is applicable to test the gas phase experiments on the identified DNT binding peptide. Vapor pressures of TNT and DNT are $0.7 \times 10^{-3}$ and $1.6 \times 10^{-3}$ mm Hg respectively under experimental conditions of 60° C. Multiple coating conditions are analyzed including: (i) DNT Receptor-OEG-Cys on gold chips, (ii) OEG-Cys on gold chips, (iii) Blank gold surface, (iv) DNT Receptor-OEG-Cys on blank silicon surface, (v) OEG-Cys on blank silicon surface, and (vi) Blank silicon surface. Immobilization of coating layers is carried out by immersing the different chips in 1 mM solution of either DNT-OEG-Cys or OEG-Cys solutions for 24 hours utilizing the available gold-thiol bond chemistry. The coatings are then exposed to target gas in ambient air by placing the chips inside a scintillation tube containing crystalline DNT or TNT which is heated uniformly to 60° C. for 2 hours using a custom designed aluminum heat block with an NIST certified temperature controller (VWR Inc., West Chester, Pa.) to generate DNT or TNT gas. Experiments are performed with chips exposed to 18 ppm of DNT gas. The chips are immediately analyzed for the amount of bound DNT and TNT by placement in the thermal desorption tube of a Unity Thermal Desorption System, which heats the chips to 300° C. and passes the desorbed particles directly to an Agilent GC-MS system (Santa Clara, Calif.). Partition coefficients are identified as the ratio of concentration of analyte bound to the coating compared to the concentration of analyte in exposed gas headspace and normalized to the appropriate control condition (ie. blank Si and OEG-Cys coatings)

Figure 7:
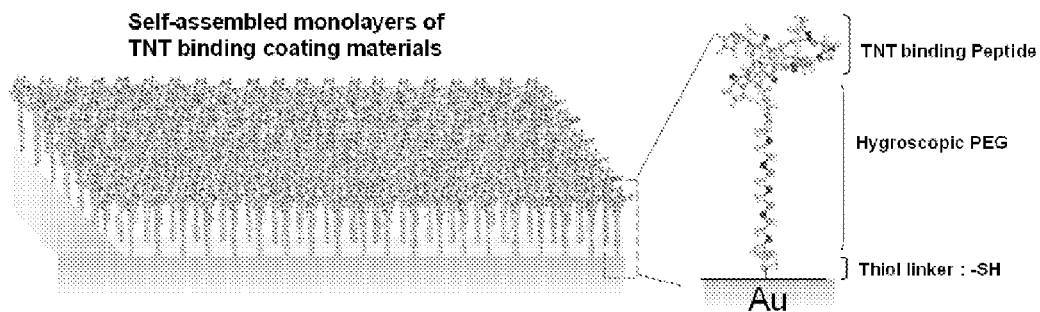
FIG. 7 shows a monolayer configuration (end-attached linear configuration) of peptide-polyethylene glycol (PEG). "TNT" can also be replaced with "DNT" or any "target molecule". "Peptide" can also be any "receptor".
Figure 8:
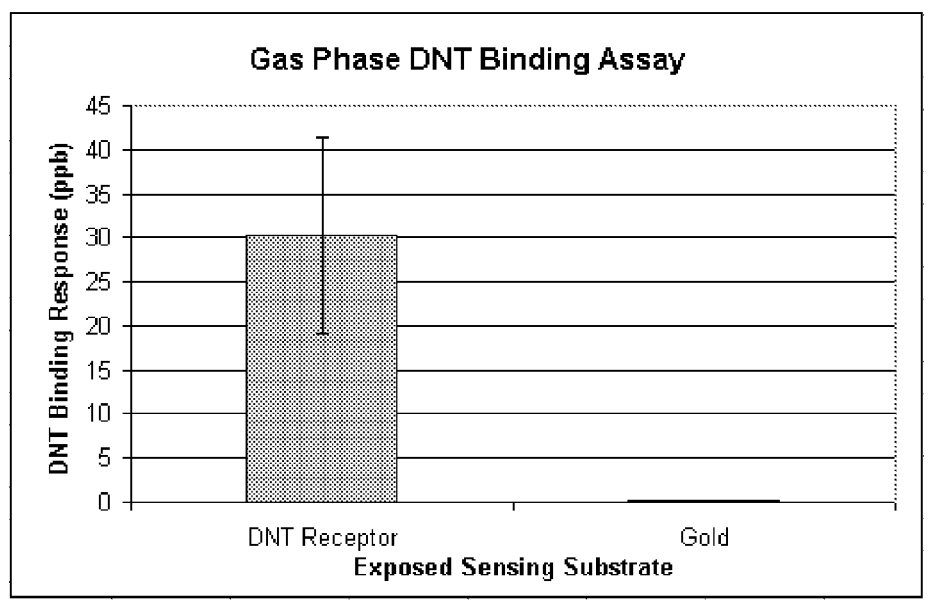
FIG. 8 shows the result of a gas phase binding assay.

A receptor that binds to DNT is synthesized with a PEG that has a thiolated C terminus monomer to facilitate attachment of the receptor-PEG molecule to a gold coated substrate. The resultant monolayer configuration is show in FIG. 7 (with "DNT" replacing "TNT"). Receptor coated gold wafers are incubated with ppm concentration of DNT gas by heating of solid DNT in a scintillation vile. The amount of bound DNT to the coating layer is analyzed via TD/GS/MS and compared to a gold only control wafers. The differential signal is in favor of a higher DNT gas binding to the DNT receptor coated chips by a factor of 8-10 as compared to the gold coated chips when normalized (see FIG. 8). The DNT receptor is able to detect DNT at about 30 parts per billion (ppb).

Figure 9:
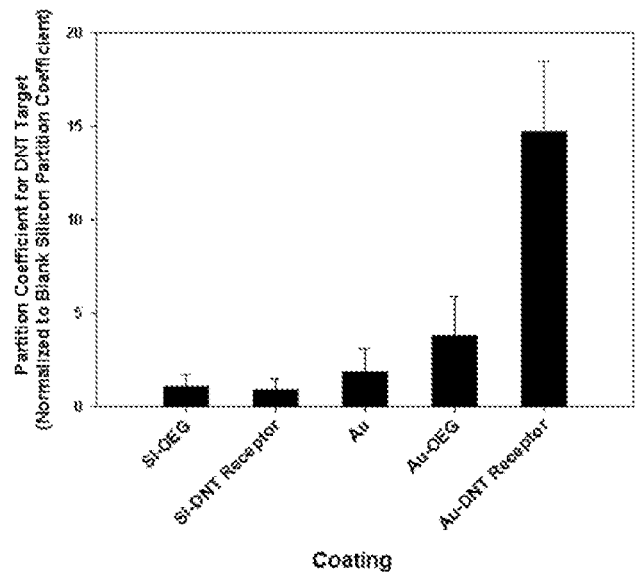
FIG. 9 shows the gas phase screening for partition coefficients of various coatings on Si exposed to DNT gas. The values are normalized to the DNT gas partition coefficient of blank Si substrates to observe the contribution attributed solely to the coating layer. Partition coefficients are calculated as the ratio of concentration of analyte bound to the coating (identified through thermal desporption GC/MS) compared to the concentration of analyte in exposed gas headspace.

The results of FIG. 9 represent the various control experiments performed to identify the extent to which DNT would interact with the various components of the Au-DNT binding peptide (BP) coating. Silicon chips are exposed to DNT gas and used as the background signal for DNT partition coefficient measurements for the various coatings of the Si chips. Six chips conditions are utilized for DNT gas experiments: (i) DNT Receptor-oligo(ethylene glycol)(OEG)-Cys on gold chips, (ii) OEG-Cys on gold chips, (iii) blank gold surface (iv) DNT Receptor-OEG-Cys on blank silicon surface, (v) OEG-Cys on blank silicon surface, and (vi) blank silicon surface (control). Importantly, the amount of DNT bound to conditions (iv) and (v) are relatively the same as that for the blank Au control (iii). This indicates the OEG-Cys or DNT Receptor-OEG-Cys coating attachment is inhibited on Si substrate as compared to their attachment to Au coated substrates under the same conditions. Furthermore, FIG. 9 identifies the highest DNT partition coefficient for condition (i) in which DNT Receptor-OEG-Cys is used as the coating for the Au chip. By displaying this comparatively large DNT partition coefficient using the DNT receptor, the ability to translate from liquid phase screened receptors into gas phase target binding is demonstrated.

Figure 10:
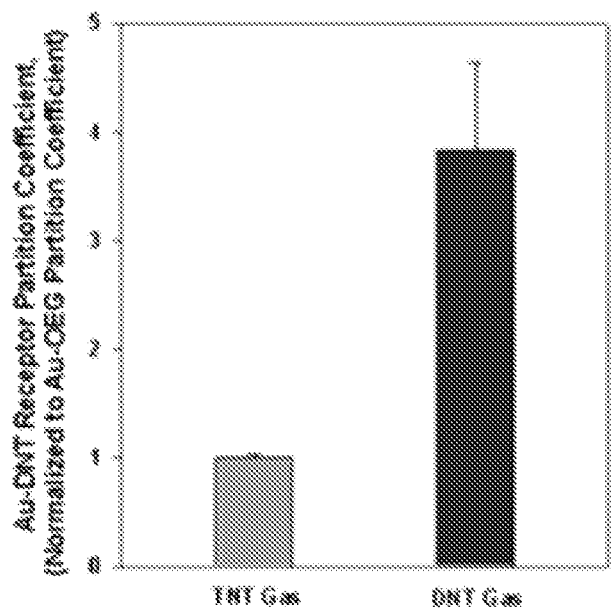
FIG. 10 shows the selective gas phase binding assay for DNT specific coating: partition coefficient of DNT receptor coatings exposed to TNT gas and DNT gas. The values are normalized to the target gas partition coefficient of oligo (ethylene glycol) (OEG) coating on Au substrate to isolate the contribution attributed to the DNT receptor element. Partition coefficients are identified as the ratio of concentration of analyte bound to the coating compared to the concentration of analyte in exposed gas headspace. Results are obtained through thermal desorption GC/MS experiments on exposed coating surfaces ($P < 0.001$, $n = 4$). All data presented as mean ±standard deviation.

The gas phase binding results for the DNT binding peptide (FIG. 10) show a 4 fold increase in the partition coefficient for DNT over TNT as a result of the DNT receptor. The preferred coating condition for selective binding of DNT gas is that of the identified DNT-BP. Additionally, the DNT-BP partition coefficient for TNT gas is on the same range as that of the OEG coated chip without a receptor indicating that the selectivity of the DNT receptor remains when implemented in gas phase.

This demonstrate that the selective coating for DNT in gas phase is of particular importance as these short OEG embedded receptors are capable of retaining efficacy outside of the liquid environment. The success of gas phase binding may be attributed to the following properties of OEG: (a) the ability of OEG to retain the conformation of biomolecules, and (b) the selectivity of peptides remaining unaffected by OEG conjugation. Additionally, PEG is often used for its non-fouling properties which may be beneficial in terms of minimizing false positives in sensing applications While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A composition comprising a receptor linked to a hygroscopic polymer wherein the receptor is capable of binding to a gaseous target molecule which is 2,4,6-trinitrotoluene (TNT) or 2,4-dinitrotoluene (DNT), wherein the receptor is a peptide which consists of the amino acid sequence selected from the group consisiting of SEQ ID NOs: 1-38 for binding to TNT, or consists of the amino acid sequence selected from the group consisiting of SEQ ID NOs: 39-66 and 68-74 for binding to DNT.

2. The composition of claim 1, wherein the hygroscopic polymer is a polyethylene glycol (PEG).

3. The composition of claim 2, wherein the PEG comprises from 1 to 30 monomers.

4. The composition of claim 1, wherein the target molecule is 2,4,6-trinitrotoluene (TNT) and the contiguous amino acid sequence is one selected from the group consisting of SEQ ID Nos: 1-38.

5. The composition of claim 1, wherein the target molecule is 2,4,-dinitrotoluene (DNT) and the contiguous amino acid sequence is one selected from the group consisting of SEQ ID Nos: 39-66 and 68-74.

* * * * *

SEQUENCE LISTING

```
<160> NUMBER OF SEQ ID NOS: 90

<210> SEQ ID NO 1
<211> LENGTH: 7
<212> TYPE: PRT
<213> ORGANISM: Artificial
<220> FEATURE:
```

<223> OTHER INFORMATION: Sequence obtained from a constructed
      combinatorial library

<400> SEQUENCE: 1

Gln His Gln Tyr Arg Met Gly
1               5

<210> SEQ ID NO 2
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 2

Leu Pro Met Thr Leu His Arg
1               5

<210> SEQ ID NO 3
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 3

Leu Thr Leu Ser Ala Gln Gly
1               5

<210> SEQ ID NO 4
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 4

Ser Gly Ala Ala Thr Arg Leu
1               5

<210> SEQ ID NO 5
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 5

Tyr Pro Asn His Pro His Arg
1               5

<210> SEQ ID NO 6
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 6

Ser Thr Ser Thr Leu Gln Lys
1               5

```
<210> SEQ ID NO 7
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 7

Tyr Pro Asn His Pro His His
1               5

<210> SEQ ID NO 8
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 8

Ser Thr Ser Thr Leu Gln Lys
1               5

<210> SEQ ID NO 9
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 9

Gly Glu Phe Asn Asn Leu Arg
1               5

<210> SEQ ID NO 10
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 10

Arg Leu Thr Asp Pro Met His
1               5

<210> SEQ ID NO 11
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 11

Thr Ala Pro Tyr Tyr Arg Asn
1               5

<210> SEQ ID NO 12
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 12
```

```
His Asn Arg Thr Thr Leu Leu
1               5

<210> SEQ ID NO 13
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 13

Asn Ala Pro Arg Thr Pro Ala
1               5

<210> SEQ ID NO 14
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 14

Thr Lys Ala His Pro Tyr His
1               5

<210> SEQ ID NO 15
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 15

Phe His Tyr Asn Asn Met His
1               5

<210> SEQ ID NO 16
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 16

Tyr Pro His Leu His Ser Asn
1               5

<210> SEQ ID NO 17
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 17

Leu Asn Met Asn His His Ser
1               5

<210> SEQ ID NO 18
<211> LENGTH: 7
<212> TYPE: PRT
<213> ORGANISM: Artificial
```

```
<220> FEATURE:
<223> OTHER INFORMATION: Sequence obtained from a constructed
      combinatorial library

<400> SEQUENCE: 18

Gln His Asn Tyr Trp Gly Thr
1               5

<210> SEQ ID NO 19
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 19

Gly His Thr Phe Leu Asp Thr
1               5

<210> SEQ ID NO 20
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 20

Ser Val Phe Met Asn Thr Pro
1               5

<210> SEQ ID NO 21
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 21

Thr Pro Asn Val Val Val Pro
1               5

<210> SEQ ID NO 22
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 22

Glu Gln Asn His Ala Tyr Phe
1               5

<210> SEQ ID NO 23
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 23

Ile Ala Gln Asn Arg Trp Ile
1               5
```

```
<210> SEQ ID NO 24
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 24

His Gln Phe Ala Asp Ile Tyr
1               5

<210> SEQ ID NO 25
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 25

Arg Thr Arg His Arg Gln Arg Thr His Ser Arg Gln
1               5                   10

<210> SEQ ID NO 26
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 26

Thr Asn Asn Phe Thr Met Thr Ser Leu Ala Pro Phe
1               5                   10

<210> SEQ ID NO 27
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 27

Thr Ser Gln Phe Thr Phe Asn Pro Pro Leu Leu Ile
1               5                   10

<210> SEQ ID NO 28
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 28

Asn Pro Pro Pro Gln Thr Glu Ala Ser Asn Ser Phe
1               5                   10

<210> SEQ ID NO 29
<211> LENGTH: 12
<212> TYPE: PRT
<213> ORGANISM: Artificial
<220> FEATURE:
<223> OTHER INFORMATION: Sequence obtained from a constructed
      combinatorial library
```

-continued

```
<400> SEQUENCE: 29

Tyr Arg Asp Ser Ser Lys Pro Tyr Leu His Tyr Pro
1               5                   10

<210> SEQ ID NO 30
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 30

Asp Trp Thr Leu Pro Ser Trp Tyr Gly Leu Pro Arg
1               5                   10

<210> SEQ ID NO 31
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 31

Asp Ser Met Tyr Lys Gln Leu Ile Ser Ala Pro Lys
1               5                   10

<210> SEQ ID NO 32
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 32

Ala Leu Gln Met Lys Gly Ser Ala Ser Ala Leu Ala
1               5                   10

<210> SEQ ID NO 33
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 33

Tyr Pro Ser Pro Met Thr Trp Leu Ala Thr Pro Phe
1               5                   10

<210> SEQ ID NO 34
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 34

Trp His Trp Gln Arg Pro Leu Met Pro Val Ser Ile
1               5                   10

<210> SEQ ID NO 35
<211> LENGTH: 12
<212> TYPE: PRT
```

<213> ORGANISM: Artificial
<220> FEATURE:
<223> OTHER INFORMATION: Sequence obtained from a constructed
      combinatorial library

<400> SEQUENCE: 35

Trp His Trp Asn Phe Lys Pro Pro His Asp Leu Leu
1               5                   10

<210> SEQ ID NO 36
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 36

Trp His Trp Ser His Arg Thr Ala Leu Tyr Thr Thr
1               5                   10

<210> SEQ ID NO 37
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 37

Trp His Trp Ser Pro Arg Thr Ala Leu Tyr Thr Thr
1               5                   10

<210> SEQ ID NO 38
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 38

Trp His Trp Lys Pro Pro Ala Pro Tyr Val Trp Trp
1               5                   10

<210> SEQ ID NO 39
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 39

Pro Ala Asn Pro Ser Arg Phe
1               5

<210> SEQ ID NO 40
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 40

Thr Gln Thr Val Thr Ser Phe
1               5

<210> SEQ ID NO 41
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 41

Trp Lys Glu Glu His Pro Gly
1               5

<210> SEQ ID NO 42
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 42

Pro Met Ala Pro Leu Trp His
1               5

<210> SEQ ID NO 43
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 43

Thr Lys Leu Thr Pro Ala Thr
1               5

<210> SEQ ID NO 44
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 44

Ser Pro Leu Ser His Pro Leu
1               5

<210> SEQ ID NO 45
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 45

Met Pro Thr Leu Phe Asn Lys
1               5

<210> SEQ ID NO 46
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 46

Pro Thr Asp Pro Gln Lys Asn
1               5

<210> SEQ ID NO 47
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 47

Ser Ile Gln Asn Thr Phe Leu
1               5

<210> SEQ ID NO 48
<211> LENGTH: 7
<212> TYPE: PRT
<213> ORGANISM: Artificial
<220> FEATURE:
<223> OTHER INFORMATION: Sequence obtained from a constructed
      combinatorial library

<400> SEQUENCE: 48

Asn Arg Pro Trp Leu Ser Thr
1               5

<210> SEQ ID NO 49
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 49

Leu His Lys Gly Pro Trp Tyr Thr Pro Tyr Pro Leu
1               5                   10

<210> SEQ ID NO 50
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 50

Leu His Lys Pro Ser Pro Arg Trp Leu Pro Val Pro
1               5                   10

<210> SEQ ID NO 51
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 51

Leu His Lys Thr Pro Gly Ser Tyr Ser Arg Trp Ser
1               5                   10

<210> SEQ ID NO 52
<211> LENGTH: 12

```
<212> TYPE: PRT
<213> ORGANISM: Artificial
<220> FEATURE:
<223> OTHER INFORMATION: Sequence obtained from a constructed
      combinatorial library

<400> SEQUENCE: 52

Tyr His Arg Thr Tyr Thr Pro Ser Tyr Asp Ser Pro
1               5                   10

<210> SEQ ID NO 53
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 53

Arg Thr Ser Ser Gly Asn Lys Thr Thr Phe Met Ser
1               5                   10

<210> SEQ ID NO 54
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 54

Lys Ile Met His Gly His Arg His Pro Leu Leu His
1               5                   10

<210> SEQ ID NO 55
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 55

Gln Pro Ala Thr Ile Ser Gly Arg Val Arg Val Cys
1               5                   10

<210> SEQ ID NO 56
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 56

Gln Arg Pro Thr Thr Gln Leu Gly Ser Glu Tyr Ala
1               5                   10

<210> SEQ ID NO 57
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 57
```

Gln Arg Pro Thr Thr Gln Gln Gly Pro Ser Met Leu
1               5                   10

<210> SEQ ID NO 58
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 58

Thr Thr Asn Ser Asp Lys Thr Gln Gly Ser Val Arg
1               5                   10

<210> SEQ ID NO 59
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 59

His Leu Asn Trp Ala Ile Ser Leu Tyr Ser Ser Pro
1               5                   10

<210> SEQ ID NO 60
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 60

His Leu Leu Tyr Ser Ala Gly Ser Ala Val Met Leu
1               5                   10

<210> SEQ ID NO 61
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 61

His Pro Asn Phe Ser Lys Tyr Ile Leu His Gln Arg
1               5                   10

<210> SEQ ID NO 62
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 62

Trp His Asn Ser Leu Trp Thr Thr Pro Thr Thr Thr
1               5                   10

<210> SEQ ID NO 63
<211> LENGTH: 12
<212> TYPE: PRT
<213> ORGANISM: Artificial
<220> FEATURE:
<223> OTHER INFORMATION: Sequence obtained from a constructed combinatorial library

<400> SEQUENCE: 63

Trp Pro His Ser His Leu Tyr Ile Arg Thr Asn Ser
1               5                   10

<210> SEQ ID NO 64
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 64

Ile His Lys His Arg Val Ser Ala Pro Ser Ile Thr
1               5                   10

<210> SEQ ID NO 65
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 65

Leu His Lys Thr Pro Gly Ser Tyr Ser Arg Trp Ser
1               5                   10

<210> SEQ ID NO 66
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 66

Val His Ser His Tyr Thr Lys His Ala Pro Phe Arg
1               5                   10

<210> SEQ ID NO 67
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 67

Trp His Arg Thr Pro Ser Thr Leu Trp Gly Val Ile
1               5                   10

<210> SEQ ID NO 68
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 68

Lys His Leu Asp Thr Ala Ser Ser Arg His Trp Asp
1               5                   10

<210> SEQ ID NO 69

-continued

```
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 69

Ala Trp Val Pro Thr Asn Thr Met Thr Thr Leu Arg
1               5                   10

<210> SEQ ID NO 70
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 70

Gln Pro Ser Glu Leu Pro Ser Ile Leu Arg Pro Leu
1               5                   10

<210> SEQ ID NO 71
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 71

Ala Thr Thr Thr Leu Pro Pro Ala Pro Phe Ala Gly
1               5                   10

<210> SEQ ID NO 72
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 72

His Ala Ser Val Pro Arg Tyr Pro His Tyr Ser Met
1               5                   10

<210> SEQ ID NO 73
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 73

Ala Ser Trp His Ser His Thr Arg Leu Asn Met His
1               5                   10

<210> SEQ ID NO 74
<211> LENGTH: 12
<212> TYPE: PRT
<213> ORGANISM: Artificial
<220> FEATURE:
<223> OTHER INFORMATION: Sequence obtained from a constructed
      combinatorial library

<400> SEQUENCE: 74
```

```
Asp Glu Gly His Gly His Trp Tyr Tyr Asp Gln Arg
1               5                  10
```

<210> SEQ ID NO 75
<211> LENGTH: 16
<212> TYPE: PRT
<213> ORGANISM: Artificial
<220> FEATURE:
<223> OTHER INFORMATION: Sequence obtained from a constructed
      combinatorial library

<400> SEQUENCE: 75

```
Trp His Trp Gln Arg Pro Leu Met Pro Val Ser Ile Gly Gly Gly Lys
1               5                  10                  15
```

<210> SEQ ID NO 76
<211> LENGTH: 4
<212> TYPE: PRT
<213> ORGANISM: Artificial
<220> FEATURE:
<223> OTHER INFORMATION: Sequence obtained from a constructed
      combinatorial library

<400> SEQUENCE: 76

```
Trp His Trp Ser
1
```

<210> SEQ ID NO 77
<211> LENGTH: 12
<212> TYPE: PRT
<213> ORGANISM: Artificial
<220> FEATURE:
<221> NAME/KEY: misc_feature
<222> LOCATION: (5)..(5)
<223> OTHER INFORMATION: Sequence obtained from a constructed
      combinatorial library; Xaa can be any naturally occurring amino
      acid

<400> SEQUENCE: 77

```
Trp His Trp Ser Xaa Arg Thr Ala Leu Tyr Thr Thr
1               5                  10
```

<210> SEQ ID NO 78
<211> LENGTH: 5
<212> TYPE: PRT
<213> ORGANISM: Artificial
<220> FEATURE:
<223> OTHER INFORMATION: Sequence obtained from a constructed
      combinatorial library

<400> SEQUENCE: 78

```
Gln Arg Pro Thr Thr
1               5
```

<210> SEQ ID NO 79
<211> LENGTH: 6
<212> TYPE: PRT
<213> ORGANISM: Artificial
<220> FEATURE:
<223> OTHER INFORMATION: Sequence obtained from a constructed
      combinatorial library

<400> SEQUENCE: 79

```
Gln Arg Pro Thr Thr Gln
1               5
```

<210> SEQ ID NO 80
<211> LENGTH: 8

```
<212> TYPE: PRT
<213> ORGANISM: Artificial
<220> FEATURE:
<221> NAME/KEY: misc_feature
<222> LOCATION: (7)..(7)
<223> OTHER INFORMATION: Sequence obtained from a constructed
      combinatorial library; Xaa can be any naturally occurring amino
      acid

<400> SEQUENCE: 80

Gln Arg Pro Thr Thr Gln Xaa Gly
1               5

<210> SEQ ID NO 81
<211> LENGTH: 8
<212> TYPE: PRT
<213> ORGANISM: Artificial
<220> FEATURE:
<223> OTHER INFORMATION: Sequence obtained from a constructed
      combinatorial library

<400> SEQUENCE: 81

Gln Arg Pro Thr Thr Gln Gln Gly
1               5

<210> SEQ ID NO 82
<211> LENGTH: 8
<212> TYPE: PRT
<213> ORGANISM: Artificial
<220> FEATURE:
<223> OTHER INFORMATION: Sequence obtained from a constructed
      combinatorial library

<400> SEQUENCE: 82

Gln Arg Pro Thr Thr Gln Leu Gly
1               5

<210> SEQ ID NO 83
<211> LENGTH: 16
<212> TYPE: PRT
<213> ORGANISM: Artificial
<220> FEATURE:
<223> OTHER INFORMATION: Sequence obtained from a constructed
      combinatorial library

<400> SEQUENCE: 83

Ala His Trp Gln Arg Pro Leu Met Pro Val Ser Ile Gly Gly Gly Lys
1               5                   10                  15

<210> SEQ ID NO 84
<211> LENGTH: 16
<212> TYPE: PRT
<213> ORGANISM: Artificial
<220> FEATURE:
<223> OTHER INFORMATION: Sequence obtained from a constructed
      combinatorial library

<400> SEQUENCE: 84

Trp Ala Trp Gln Arg Pro Leu Met Pro Val Ser Ile Gly Gly Gly Lys
1               5                   10                  15

<210> SEQ ID NO 85
<211> LENGTH: 16
<212> TYPE: PRT
<213> ORGANISM: Artificial
<220> FEATURE:
<223> OTHER INFORMATION: Sequence obtained from a constructed
      combinatorial library
```

```
<400> SEQUENCE: 85

Trp His Ala Gln Arg Pro Leu Met Pro Val Ser Ile Gly Gly Gly Lys
1               5                   10                  15

<210> SEQ ID NO 86
<211> LENGTH: 16
<212> TYPE: PRT
<213> ORGANISM: Artificial
<220> FEATURE:
<223> OTHER INFORMATION: Sequence obtained from a constructed
      combinatorial library

<400> SEQUENCE: 86

Trp His Trp Ala Arg Pro Leu Met Pro Val Ser Ile Gly Gly Gly Lys
1               5                   10                  15

<210> SEQ ID NO 87
<211> LENGTH: 16
<212> TYPE: PRT
<213> ORGANISM: Artificial
<220> FEATURE:
<223> OTHER INFORMATION: Sequence obtained from a constructed
      combinatorial library

<400> SEQUENCE: 87

Trp His Trp Gln Ala Pro Leu Met Pro Val Ser Ile Gly Gly Gly Lys
1               5                   10                  15

<210> SEQ ID NO 88
<211> LENGTH: 10
<212> TYPE: PRT
<213> ORGANISM: Artificial
<220> FEATURE:
<223> OTHER INFORMATION: Sequence obtained from a constructed
      combinatorial library

<400> SEQUENCE: 88

Trp His Trp Gln Arg Pro Gly Gly Gly Lys
1               5                   10

<210> SEQ ID NO 89
<211> LENGTH: 16
<212> TYPE: PRT
<213> ORGANISM: Artificial
<220> FEATURE:
<223> OTHER INFORMATION: Sequence obtained from a constructed
      combinatorial library

<400> SEQUENCE: 89

Leu Pro Ser Met Arg Val Trp Pro Gln Trp Ile His Gly Gly Gly Lys
1               5                   10                  15

<210> SEQ ID NO 90
<211> LENGTH: 16
<212> TYPE: PRT
<213> ORGANISM: Artificial
<220> FEATURE:
<223> OTHER INFORMATION: Sequence obtained from a constructed
      combinatorial library

<400> SEQUENCE: 90

Trp His Arg Thr Pro Ser Thr Leu Trp Gly Val Ile Gly Gly Gly Lys
1               5                   10                  15
```